(12) United States Patent
Zhu et al.

(10) Patent No.: US 12,296,466 B2
(45) Date of Patent: May 13, 2025

(54) ROBOTIC ARM

(71) Applicant: BEIJING ROSSUM ROBOT TECHNOLOGY CO., LTD, Haidian Beijing District (CN)

(72) Inventors: Gang Zhu, Haidian Beijing (CN); Kewen Mu, Haidian Beijing (CN); Ke Xu, Haidian Beijing (CN); Wei Tian, Haidian Beijing (CN); Xiangrui Zhao, Haidian Beijing (CN)

(73) Assignee: BEIJING ROSSUM ROBOT TECHNOLOGY CO., LTD, Haidian Beijing (CN)

( * ) Notice: Subject to any disclaimer, the term of this patent is extended or adjusted under 35 U.S.C. 154(b) by 0 days.

(21) Appl. No.: 18/546,443

(22) PCT Filed: May 5, 2022

(86) PCT No.: PCT/CN2022/090970
§ 371 (c)(1),
(2) Date: Aug. 15, 2023

(87) PCT Pub. No.: WO2023/115782
PCT Pub. Date: Jun. 29, 2023

(65) Prior Publication Data
US 2024/0116197 A1    Apr. 11, 2024

(30) Foreign Application Priority Data

Dec. 23, 2021 (CN) .......................... 202111587900.7

(51) Int. Cl.
*B25J 17/02* (2006.01)
*B25J 18/00* (2006.01)
*B25J 19/00* (2006.01)

(52) U.S. Cl.
CPC ........... *B25J 17/0275* (2013.01); *B25J 18/00* (2013.01); *B25J 19/0004* (2013.01)

(58) Field of Classification Search
None
See application file for complete search history.

(56) References Cited

U.S. PATENT DOCUMENTS 10,357,330 B2 *    7/2019    Fukushima ............ A61B 90/50
2005/0075536 A1    4/2005    Otsuka et al.

FOREIGN PATENT DOCUMENTS

CN         101703423 A      5/2010
CN         206551006 U     10/2017
(Continued)

*Primary Examiner* — Vicky A Johnson
(74) *Attorney, Agent, or Firm* — FISHERBROYLES, LLP; Roger L. Browdy; James E. Mrose

(57) ABSTRACT

The present invention relates to a robotic arm, including: an upper arm and a front arm; a first joint structure, by which the upper arm and the front arm are articulated together; a second joint structure, arranged at an end of the upper arm and/or an end of the front arm; a first driving mechanism, arranged in the upper arm; and a second driving mechanism, arranged in the front arm, where the first joint structure includes a first force amplification apparatus and a first locking element, the second joint structure includes a second force amplification apparatus and a second locking element, and the first driving mechanism and the second driving mechanism apply an acting force to the first locking element and/or the second locking element by the first force amplification apparatus and/or the second force amplification apparatus. According to the robotic arm in the present invention, the force amplification apparatuses are arranged in the joint structures, which amplifies a locking force and enables the robotic arm to meet the requirements for large load applications under a miniature condition.

10 Claims, 3 Drawing Sheets

(56) References Cited

FOREIGN PATENT DOCUMENTS

| CN | 109676595 | A | * | 4/2019 | ................ | B25J 9/06 |
| CN | 212241113 | U | | 12/2020 | | |
| CN | 212978396 | U | | 4/2021 | | |
| CN | 112826591 | A | | 5/2021 | | |
| CN | 214265648 | U | | 9/2021 | | |

* cited by examiner

ROBOTIC ARM

TECHNICAL FIELD

The present invention belongs to the field of medical technologies, and relates to a robotic arm for a surgery.

BACKGROUND

In recent years, with the continuous development of medical robot technologies at home and abroad, medical robots have become an important branch in the field of robots and also an important research direction in the field of biomedical engineering. In the medical field, especially in the field of surgical robots, the surgical robots can perform some complex surgical actions by accurately controlling the operations of robotic arms. In addition, there are also demands for fixing and holding limbs, surgical tools, etc. in the medical field, and the demand for a holding force is higher. Therefore, for existing medical instruments, different passive arms are designed according to different holding requirements. Whether it is an active or passive robotic arm, it usually has a plurality of joints, so that multi-degree-of-freedom adjustment can be implemented.

One of the core technologies for robotic arms is a joint locking mechanism, which mainly adopts hydraulic, pneumatic, electric, mechanical and other driving modes at present. A joint locking mechanism for pure mechanical locking requires manual locking, and when a state of a robotic arm needs to be adjusted, manual unlocking is also required, which increases the operation intensity of a doctor. However, under a miniature condition, there are a small locking force in other modes and a low load for the robotic arm after locking, which cannot meet the requirements for larger load applications.

SUMMARY

To increase a locking force of a robotic arm and meet the requirements for larger load applications, the present invention provides a robotic arm, including:
an upper arm and a front arm;
a first joint structure, wherein the upper arm and the front arm are articulated together by the first joint structure;
a second joint structure, arranged at an end of the upper arm and/or an end of the front arm;
a first driving mechanism, arranged in the upper arm; and
a second driving mechanism, arranged in the front arm,
where the first joint structure includes a first force amplification apparatus and a first locking element, the second joint structure includes a second force amplification apparatus and a second locking element, and the first driving mechanism and the second driving mechanism apply an acting force to the first locking element and/or the second locking element by the first force amplification apparatus and/or the second force amplification apparatus.

Further, the first joint structure includes:
a first joint head and a second joint head; and
an articulated shaft, where the first joint head and the second joint head are connected by the articulated shaft;
the first locking element is arranged between the first joint head and the second joint head and is configured to lock the first joint head and the second joint head; and
the first force amplification apparatus is arranged on one side and/or two sides of the first locking element and is configured to apply an amplified acting force to the first locking element.

Further, the second joint structure includes:
a joint housing; and
a third joint head, arranged in the joint housing,
where the second locking element is arranged in contact with the third joint head and is configured to lock the third joint head; and
the second force amplification apparatus is arranged at one end of the second locking element and is configured to apply an amplified acting force to the second locking element.

Further, a structure being at least partially spherical is provided at one end of the third joint head, and a spherical structure being partially recessed inwards is provided at one end of the second locking element and cooperates with a portion in contact with the third joint head.

Further, the first force amplification apparatus and/or the second force amplification apparatus are/is of a lever type structure.

Further, the first force amplification apparatus includes a first rotary shaft and a first force amplification rod arranged on the first rotary shaft, where a distance between a force receiving end of the first force amplification rod and the first rotary shaft is greater than a distance between a force applying end of the first force amplification rod and the first rotary shaft.

Further, the second force amplification apparatus includes two second force amplification rods connected together by a second rotary shaft, where a distance between a force receiving end of each of the second force amplification rods and the second rotary shaft is greater than a distance between a force applying end of the second force amplification rod and the second rotary shaft.

Further, the first locking element includes two or more friction plates sleeved on the articulated shaft.

Further, a ball joint pin is provided at the other end of the third joint head and extends out of the joint housing.

Further, the driving mechanism is one of a telescopic rod, an electric push rod, a lead screw, a hydraulic cylinder, and a pneumatic cylinder.

According to the robotic arm in the present invention, the force amplification apparatuses are arranged in the joint structures, which amplifies the locking force and enables the robotic arm to meet the requirements for large load applications under miniature conditions.

The force amplification apparatus may adopt a lever mode, and a distance from the force receiving end to an articulated point is greater than a distance from the articulated point to the force applying end, which can amplify the acting force on the force receiving end and then apply a greater force to the locking element at the force applying end, thereby achieving a good locking effect.

In addition to the technical problems solved by the present invention, the technical features of the formed technical solutions, and the advantages brought by the technical features of these technical solutions described above, other technical features of the present invention and the advantages brought by these technical features will be further described in conjunction with the accompanying drawings.

BRIEF DESCRIPTION OF THE DRAWINGS

To more clearly illustrate the technical solutions in the embodiments of the present invention or in the prior art, the accompanying drawings that need to be used in the description of the embodiments or the prior art will be briefly described below. Apparently, the accompanying drawings in the description below merely illustrate some embodiments of the present invention. Those of ordinary skill in the art may also derive other accompanying drawings from these accompanying drawings without creative efforts.

In the drawings.

Figure 1:
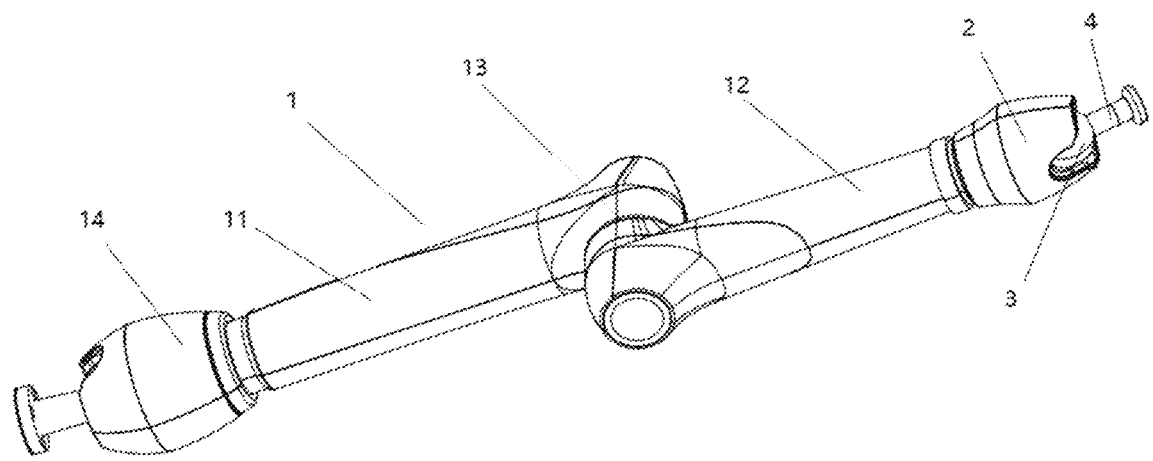
FIG. 1 is a schematic structural diagram of a robotic arm according to the present invention.

1. robotic arm; 11. upper arm; 12. front arm; 13. first joint structure; 14. second joint structure; 2. ball joint housing; 3. ball joint; 4. ball joint pin; 5. ball bowl; 6. second force amplification rod; 7. second rotary shaft; 8. robotic arm housing; 9. raised head; 20. first joint head; 21. second joint head; 22. articulated shaft; 23. first locking element; 24. first rotary shaft; 25. first force amplification rod; 26. slide block; 27. stop piece; 28. ejector block; 29. first driving apparatus; and 30. spring.

DETAILED DESCRIPTION OF THE EMBODIMENTS

In the description of the embodiments of the present invention, it should be noted that the orientations or positional relationships indicated by the terms "center", "longitudinal", "transverse", "upper", "lower", "front", "back", "left", "right", "vertical", "horizontal", "top", "bottom", "inside", "outside", etc. are based on the orientations or positional relationships shown in the accompanying drawings, are only for the convenience of describing the embodiments of the present invention and simplifying the description rather than indicating or implying that the apparatus or element referred to must have a specific orientation or be constructed and operated in a specific orientation, and therefore should not be construed as a limitation to the embodiments of the present invention. Furthermore, the terms "first", "second", and "third" are merely used for descriptive purposes and should not be understood to indicate or imply relative importance.

In the description of the embodiments of the present invention, it should be noted that the terms "connected" and "connection" should be understood in a broad sense, unless otherwise expressly specified and defined. For example, the "connection" may be a fixed connection, a detachable connection, or an integrated connection; the "connection" may also be a mechanical connection or an electrical connection; and the "connected" may be directly connected or indirectly connected via an intermediate medium. Those of ordinary skill in the art may understand the specific meanings of the above terms in the embodiments of the present invention according to the specific circumstances.

The present invention provides a robotic arm, including:
an upper arm and a front arm;
a first joint structure, where the upper arm and the front arm are articulated together by the first joint structure;
a second joint structure, arranged at an end of the upper arm and/or an end of the front arm;
a first driving mechanism, arranged in the upper arm; and
a second driving mechanism, arranged in the front arm,
where the first joint structure includes a first force amplification apparatus and a first locking element, the second joint structure includes a second force amplification apparatus and a second locking element, and the first driving mechanism and the second driving mechanism apply an acting force to the first locking element and/or the second locking element by the first force amplification apparatus and/or the second force amplification apparatus.

According to the robotic arm in the present invention, the force amplification apparatuses are arranged in the joint structures, respectively. In a case where driving apparatuses apply a same locking force, the force amplification apparatuses are added, so that the locking force of the robotic arm is greatly increased and the requirements for larger load applications are met. Especially under a miniature condition of the robotic arm, the robotic arm can be locked electrically or pneumatically, which improves the use convenience of an operator compared with mechanical locking.

Optionally, the first driving mechanism is arranged in the upper arm and can simultaneously provide a driving force to two ends. For example, the first driving mechanism can simultaneously apply the acting force to a force receiving end of the first force amplification apparatus in the first joint structure at one end and a force receiving end of the second force amplification apparatus in the second joint structure at the other end. Optionally, the second driving mechanism is arranged in the front arm and can also simultaneously provide a driving force to two ends. For example, the second driving mechanism can simultaneously apply the acting force to the force receiving end of the first force amplification apparatus in the first joint structure at one end and the force receiving end of the second force amplification apparatus in the second joint structure at the other end. When both the first driving mechanism and the second driving mechanism apply the acting force to the force receiving end of the first force amplification apparatus in the first joint structure, two first force amplification apparatuses are arranged in the first joint structure, where the two first force amplification apparatuses are arranged on two sides of the first locking element, respectively. When either the first driving mechanism or the second driving mechanism applies the acting force to the force receiving end of the first force amplification apparatus in the first joint structure, one first force amplification apparatus is arranged in the first joint structure, where the first force amplification apparatus is arranged on one side of the first locking element and is close to one side of the corresponding driving apparatus that provides a driving force.

Further, the first joint structure includes: a first joint head and a second joint head; and an articulated shaft, where the first joint head and the second joint head are connected by the articulated shaft; the first locking element is arranged between the first joint head and the second joint head and is configured to lock the first joint head and the second joint head; and the first force amplification apparatus is arranged on one side and/or two sides of the first locking element and is configured to apply an amplified acting force to the first locking element.

The first joint structure in the present invention is configured to connect two arms to serve as a joint between the two arms. During use, the first joint structure is released first, and after the robotic arm is adjusted to reach a suitable position, the driving mechanisms can quickly lock the robotic arm and provide a larger locking load. Compared with conventional mechanical connection and locking, the advantages of more convenience in mounting and positioning, and faster locking are achieved.

Preferably, the first force amplification apparatus may be of a lever type structure. The lever type force amplification apparatus has a simple structure. By setting a proportional relationship between force arms, a multiple of force amplification is easily adjusted, and a force amplification effect is remarkable.

The first force amplification apparatus may include a first rotary shaft and a first force amplification rod, where a distance between a force receiving end of the first force amplification rod and the first rotary shaft is greater than a distance between a force applying end of the first force amplification rod and the first rotary shaft. Therefore, the acting force on the force receiving end may be amplified at the force applying end and then applied to the first locking element.

Optionally, one first force amplification apparatus may be arranged on one side of the first locking element, and has the force applying end abutting against one side of the first locking element and the force receiving end connected to the corresponding driving apparatus. Alternatively, one first force amplification apparatus may be arranged on each of two sides of the first locking element, and the force receiving end of each first force amplification apparatus is connected to a first driving apparatus or a second driving apparatus. Or optionally, the force receiving end of one of the first force amplification apparatuses is connected to the corresponding driving apparatus, and the force receiving end of the other one abuts against an inner wall of the corresponding joint head.

Preferably, the first locking element includes a plurality of friction plates sleeved on the articulated shaft. The friction plates may be made of a rubber material, and a coefficient of friction of the material and the number of friction plates may be selected according to a load that needs to be borne.

Optionally, one end of the articulated shaft may be fixedly arranged on one of the first joint head and the second joint head, and the other joint head is articulated on the articulated shaft, so that relative rotation between the first and second joint heads can be implemented. Alternatively, both the first and second joint heads are articulated on the articulated shaft, and the two joint heads may both rotate about the articulated shaft and may rotate relative to each other. Those skilled in the art may choose a specific mounting form according to a requirement.

Preferably, the first joint structure includes a stop piece sleeved at an end of the articulated shaft and embedded at an end of the first joint head and/or an end of the second joint head. A connection manner for the stop piece allows for relative rotation between the first and second joint heads, while preventing the two joint heads from separating from the end of the articulated shaft.

Optionally, the first joint structure further includes a slide block sleeved on the articulated shaft and located between the first locking element and the first force amplification apparatus. The slide block is movable along the articulated shaft, and the force applying end of the first force amplification apparatus abuts against the slide block, which facilitates the uniform application of the acting force on the first locking element. The force applying end does not directly apply the acting force to the first locking element, which can prevent damage to the first locking element due to excessive local stress.

Preferably, an arc-shaped end surface protruding outwards is provided at the force applying end of the first force amplification rod. The arc-shaped end surface is in contact with the slide block, which makes it easier to generate relative movement and facilitates the application of the acting force; and the slide block is pushed to move along the articulated shaft, so as to press the first locking element tightly.

Further, the first joint structure further includes an ejector block slidably arranged in a cavity of the first joint head and/or a cavity of the second joint head. The ejector block has a bottom end in contact with the corresponding driving apparatus and a top end in contact with the force receiving end of the first force amplification apparatus. The ejector block is mainly configured to transfer an acting force of the corresponding driving apparatus to the force receiving end of the first force amplification apparatus. Preferably, the top end of the ejector block is in point contact with the force receiving end of the first force amplification apparatus. For example, the top end of the ejector block is of a spherical structure, and an arc-shaped end surface is provided at the force receiving end of the first force amplification apparatus, so that the point contact can be formed between the top end of the ejector block and the force receiving end of the first force amplification apparatus. The spherical structure and the arc-shaped end surface are in contact with each other and are prone to relative movement, so that the force receiving end of the first force amplification apparatus is caused to rotate about the rotary shaft to drive the force applying end to move towards the slide block or the first locking element, so as to apply the acting force.

Further, the second joint structure includes: a joint housing; and a third joint head arranged in the joint housing, where the second locking element is arranged in contact with the third joint head and is configured to lock the third joint head; and the second force amplification apparatus is arranged at one end of the second locking element and is configured to apply an amplified acting force to the second locking element.

Further, the second force amplification apparatus is of a lever type structure. The lever type force amplification apparatus has a simple structure. By setting a proportional relationship between force arms, a multiple of force amplification is easily adjusted, and a force amplification effect is remarkable.

Preferably, the second force amplification apparatus includes a second rotary shaft and a second force amplification rod arranged on the second rotary shaft, where a distance between a force receiving end of the second force amplification rod and the second rotary shaft is greater than a distance between a force applying end of the second force amplification rod and the second rotary shaft. The second rotary shaft may be arranged on the housing, so that the second force amplification rod may rotate about the second rotary shaft. A distance from the force receiving end to an articulated point is greater than a distance from the articulated point to the force applying end, which can amplify the acting force on the force receiving end and then apply a greater acting force to the locking element at the force applying end, thereby achieving a good locking effect.

More preferably, the second force amplification apparatus includes two second force amplification rods connected together by a second rotary shaft. For example, the two second force amplification rods are connected together by the second rotary shaft to form a structure similar to a form of scissors. In this case, the second rotary shaft does not need to be arranged on the housing.

Preferably, an arc-shaped end surface is provided at the force receiving end of the second force amplification rod.

Cooperatively, an arc-shaped end surface is also provided at a portion, in contact with the force receiving end of the second force amplification rod, of the corresponding driving mechanism, and point contact can be formed between the arc-shaped end surface and the force receiving end of the second force amplification rod, which facilitates relative movement. In addition, the arc-shaped end surface may have a certain inclination angle or an inwards recessed radian, which can enable an end of the corresponding driving mechanism to make preset relative movement along the force receiving end of the second force amplification rod, resulting in preset rotation at the force receiving end of the second force amplification rod.

Preferably, an arc-shaped end surface protruding outwards is provided at the force applying end of the second force amplification rod. The arrangement of the arc-shaped end surface facilitates relative movement between the force applying end and the second locking element, so as to apply the amplified acting force to the second locking element. Moreover, the arrangement of the arc-shaped end surface protruding outwards can enable the force applying end to press the second locking element tightly during relative movement between the force applying end and the second locking element.

Preferably, a structure being at least partially spherical is provided at one end of the third joint head. A spherical structure being partially recessed inwards is provided at one end of the second locking element and cooperates with a portion in contact with the third joint head.

Preferably, a ball joint pin is provided at the other end of the third joint head 32 and extends out of the joint housing. The ball joint pin can be configured to be connected to an auxiliary tool or a fixing tool.

Preferably, a plurality of U-shaped openings are provided on a side wall of the joint housing. The ball joint pin can rotate into the U-shaped openings, so as to expand the range of movement and degree of freedom of the ball joint pin.

The second joint structure in the present invention amplifies a locking force of a joint by the second force amplification apparatus, so that the second joint structure can be used for a passive robotic arm and a robotic arm of a surgical robot.

When third joint structures in the present invention are arranged at two ends of the robotic arm, the first driving apparatus and the second driving apparatus provide locking forces for the third joint structures at the two ends, respectively. In this case, the robotic arm has at least six degrees of freedom, allowing it to provide flexible movement of surgical tools in space with arbitrary degree of freedom. After the robotic arm reaches the suitable position, the driving mechanisms can quickly lock the robotic arm and provide the larger locking load. Compared with conventional mechanical connection and locking, the robotic arm has the advantages of more convenience in mounting and positioning, and faster locking.

Certainly, the above third joint structure may also be arranged only at one end of the robotic arm.

Further, the driving mechanism may be one of a telescopic rod, an electric push rod, a lead screw, a hydraulic cylinder, and a pneumatic cylinder. Preferably, the driving mechanism is the electric push rod convenient for a user to control.

In addition, the first and second driving mechanisms may be controlled by external switches. A controller may be connected to an exterior of the robotic arm, and the switches (foot switches, key switches, or more complicated switches) are arranged to send external signals to control the driving mechanisms. The driving mechanisms can provide thrusts to the joint structures at the two ends and the locking forces are amplified by the force amplification apparatuses, so that the joint structures are pushed to be quickly locked; and the switches may also control the driving mechanisms to retract, so that the thrusts are reduced to release the joints of the robotic arm.

To more clearly understand the objective, features and advantages of the present invention, the present invention is further described in detail below in conjunction with the accompanying drawings and the specific embodiments. It should be noted that the embodiments of the present application and the features in the embodiments can be combined with each other if there is no conflict.

FIG. 1 is a schematic structural diagram of a robotic arm. As shown in FIG. 1, a robotic arm 1 includes an upper arm 11 and a front arm 12 articulated to each other by a first joint structure 13.

In this embodiment, second joint structures 14 are arranged at two ends of the robotic arm 1, respectively. In practical application, the upper arm 11 of the robotic arm 1 is configured to be fixed to equipment such as an operating table and a surgical trolley, and the front arm 12 is configured to be connected to a surgical tool or to fix a limb. In this embodiment, the upper arm 11 and the front arm 12 include an upper arm body and a front arm body, respectively, and the upper arm body and the front arm body include a first driving mechanism and a second driving structure, respectively, which are configured to provide locking forces for the joint structures. The driving mechanisms in this embodiment may be electric or pneumatic mechanisms, preferably electric push rods. Compared with a robotic arm of mechanical joint locking, it is easier to electrically lock the joints of the robotic arm.

Figure 2:
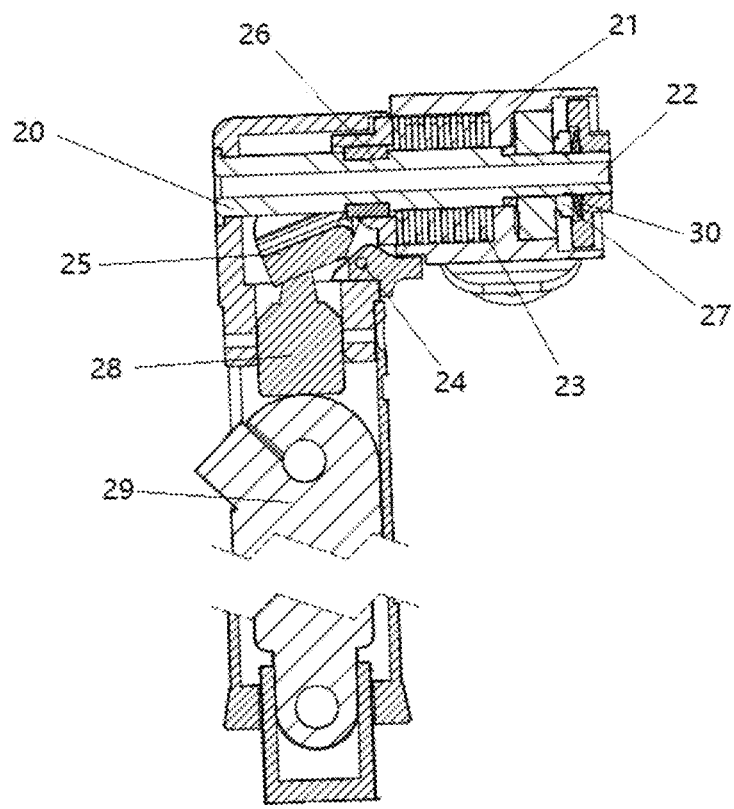
FIG. 2 is a sectional view of a first joint structure according to an embodiment of the present invention.

As shown in FIG. 1 and FIG. 2, the first joint structure 13 in this embodiment is arranged between the upper arm 11 and the front arm 12, a first joint head 20 is arranged at an end of the upper arm 11, and a second joint head 21 is arranged at an end of the front arm 12. The first joint head 20 and the second joint head 21 are articulated together by an articulated shaft 22, thereby allowing for relative rotation between the first joint head 20 and the second joint head 21.

In this embodiment, the articulated shaft 22 is fixedly arranged on the first joint head 20, the second joint head 21 is articulated on the articulated shaft 22, and a stop piece 27 is arranged at an end of the articulated shaft 22, embedded in a groove at an end of the second joint head 21, and configured to prevent the second joint head 21 from falling off the articulated shaft 22.

In this embodiment, a spring 30 is arranged at the end of the articulated shaft 22. The spring 30 is sleeved on the articulated shaft 22, has two ends abutting against an end of the stop piece 27 and the end of the second joint head 21, respectively, and can provide a pre-pressure between the first joint head 20 and the second joint head 21, so that the joints will not excessively relax in an unlocked state.

A first locking element 23 is arranged between the first joint head 20 and the second joint head 21. In this embodiment, a plurality of friction plates are used as the first locking element 23 and are sleeved on the articulated shaft 22.

The first joint structure 13 in this embodiment further includes a first force amplification apparatus. In this embodiment, the first force amplification apparatus is of a lever type structure, and includes a first force amplification rod 25 and a first rotary shaft 24, where two ends of the first rotary shaft 24 may be arranged on inner walls of the joint heads, and the first force amplification rod 25 can rotate about the first rotary shaft 24. A distance from a force receiving end of the first force amplification rod 25 to the first rotary shaft 24 is greater than a distance from a force applying end of the first force amplification rod 25 to the first rotary shaft 24. In this embodiment, one first force amplification apparatus is arranged in the first joint head 20.

The first joint structure 13 in this embodiment further includes a slide block 26 sleeved on the articulated shaft 22 and located between the first force amplification apparatus and the first locking element 23. The force applying end of the first force amplification rod 25 abuts against the slide block 26 and applies an acting force to the first locking element 23 by the slide block 26.

A first driving apparatus 29 is arranged in the upper arm 11. In this embodiment, an electric push rod is used as the first driving apparatus 29. An ejector block 28 is arranged at a top end of the driving apparatus 29, and a top of the ejector block 28 is spherical and abuts against the force receiving end of the first force amplification rod 25.

When the first joint structure 13 needs to be locked, the driving apparatus 29 rotates, the ejector block 28 moves towards the force receiving end of the first force amplification rod 25, the force receiving end of the first force amplification rod 25 receives the acting force and then rotates about the first rotary shaft 24, the force applying end of the first force amplification rod 25 applies an amplified acting force to an end of the slide block 26, the slide block 26 moves (without rotation) along the articulated shaft 22, and a locking force is applied to a surface of the first locking element 23, so as to lock the first joint structure 13. In this case, there is no rotation between the first joint head 20 and the second joint head 21. When the first joint structure 13 needs to be released, the electric push rod rotates reversely, and the ejector block 28 moves in a direction away from the force receiving end of the first force amplification rod 25, to reduce or cancel the acting force applied to the force receiving end of the first force amplification rod 25, so as to reduce or cancel the acting force on the end of the slide block 26. In this case, the first joint head 20 and the second joint head 21 are unlocked and can rotate relatively.

Preferably, the first force amplification rod 25 is of a sheet structure, and an arc-shaped end surface recessed inwards may be provided at the force receiving end of the first force amplification rod. Cooperatively, an end of the ejector block 28 is a spherical surface, so that point contact can be formed between the ejector block 28 and the force receiving end of the first force amplification rod 25, which facilitates relative movement. Moreover, an end surface of the force receiving end of the first force amplification rod 25 may have a certain inclination angle, so that the end of the ejector block 28 can easily make relative movement along the force receiving end of the first force amplification rod 25 when moving towards the first force amplification rod 25. Preferably, an arc-shaped end surface protruding outwards is provided at the force applying end of the first force amplification rod 25. The arrangement of the arc-shaped end surface facilitates relative movement between the force applying end and the slide block 26, so as to apply the amplified acting force to the first locking element 23.

Figure 3:
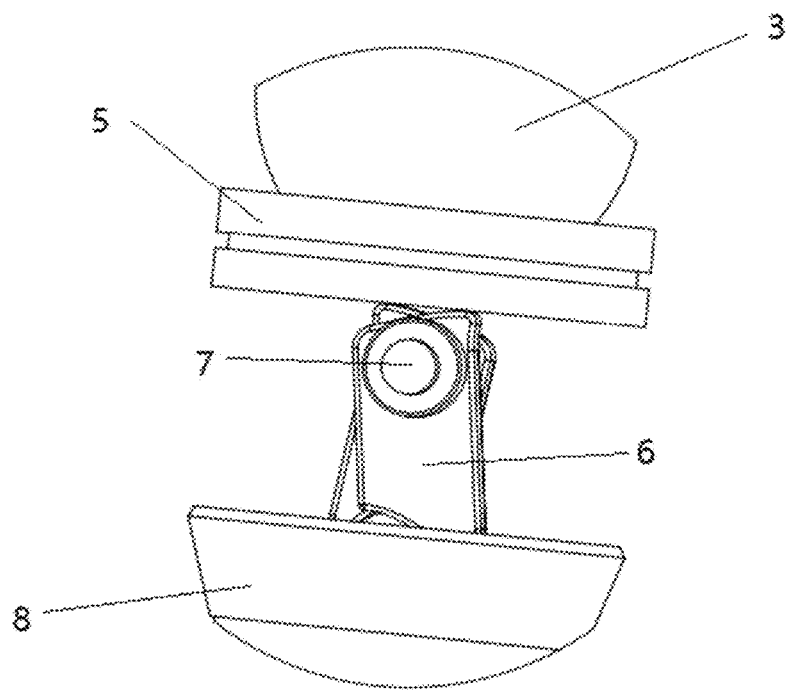
FIG. 3 is a schematic diagram of a second force amplification apparatus according to an embodiment of the present invention.
Figure 4:
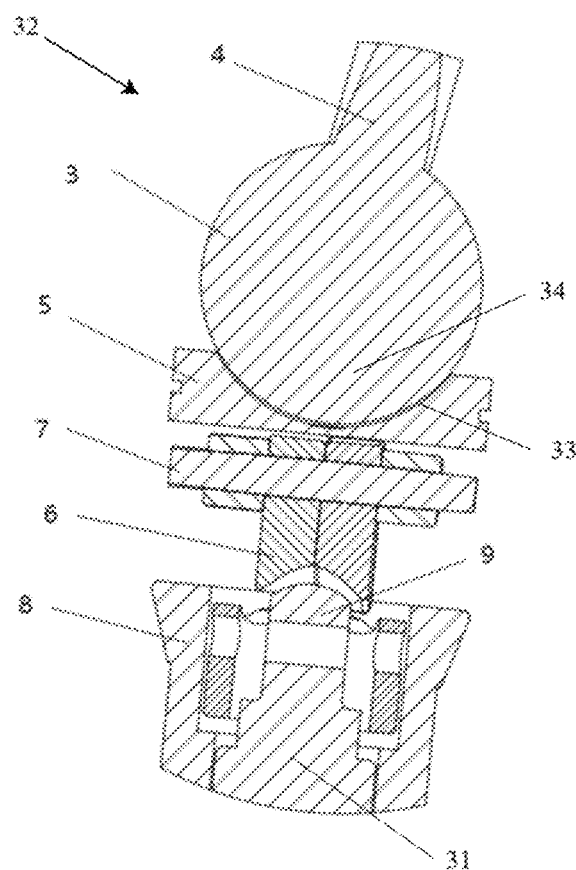
FIG. 4 is a sectional view of a second joint structure according to an embodiment of the present invention, and shows a sectional view of connection between a second force amplification apparatus and a driving apparatus.

As shown in FIG. 3 and FIG. 4, the second joint structures 14 in this embodiment are arranged at the end of the upper arm 11 and the end of the front arm 12, and each includes a ball joint housing 2 and a ball joint 3, where one spherical end 34 of the ball joint 3 is rotatably arranged in the ball joint housing 2, and a ball joint pin 4 is arranged at the other end of the ball joint 3 and configured to be connected to a surgical tool or to fix the tool. The ball joint housing 2 is provided with an opening for the ball joint pin 4 to penetrate through, and has a U-shaped opening, which expands the range of movement of the ball joint pin 4. The joint structure further includes a ball bowl 5 arranged on the spherical end of the ball joint 3, where the ball bowl 5 has a partially inwards recessed spherical surface 33 matched in shape with the ball joint 3.

The second joint structure 14 in this embodiment further includes a second force amplification apparatus. In this embodiment, the second force amplification apparatus is of a lever type structure, and includes a pair of second force amplification rods 6 articulated together by a second rotary shaft 7. A force applying end of the second force amplification rod 6 is close to an end of the ball bowl 5 and is used to apply an acting force to the ball bowl 5. A force receiving end of the second force amplification rod 6 is in contact with a raised head 9 of the driving apparatus 31. The driving apparatus 31 is the electric push rod arranged in a robotic arm housing 8.

When the second joint structure 14 needs to be locked, the electric push rod rotates, the raised head 9 moves towards the force receiving end of the second force amplification rod 6, the force receiving end of the second force amplification rod 6 receives the acting force and then amplifies the acting force by a lever, the force applying end of the second force amplification rod 6 applies an amplified acting force to the end of the ball bowl 5, the ball bowl 5 applies a locking force to a surface of the ball joint 3, so as to lock the second joint structure 14. When the second joint structure 14 needs to be released, the electric push rod rotates reversely, and the raised head 9 moves in a direction away from the force receiving end of the second force amplification rod 6, to reduce or cancel the acting force applied to the force receiving end of the second force amplification rod 6, so as to reduce or cancel the acting force on the end of the ball bowl 5. In this case, the ball joint 3 is movable relative to the ball bowl 5.

In this embodiment, as shown in figure, the second force amplification rod 6 is of a sheet structure, and an arc-shaped end surface recessed inwards is provided at the force receiving end of the second force amplification rod. Cooperatively, an end of the raised head 9 of the electric push rod is a spherical surface, so that point contact can be formed between the raised head 9 and the force receiving end of the second force amplification rod 6, which facilitates relative movement. Moreover, an end surface of the force receiving end of the second force amplification rod 6 may have a certain inclination angle, so that the end of the raised head 9 can easily make relative movement along the force receiving end of the second force amplification rod 6 when moving towards the second force amplification rod 6; and the force receiving ends of the two second force amplification rods 6 get away from each other, so that the movement closer to the ball bowls 5 is produced at the force applying ends of the two second force amplification rods 6, and the amplified acting force is applied to the ball bowls 5. In this embodiment, an arc-shaped end surface protruding outwards is provided at the force applying end of the second force amplification rod 6. The arrangement of the arc-shaped end surface facilitates relative movement between the force applying end and the ball bowl 5, so as to apply the amplified acting force to the ball bowl 5.

In this embodiment, the robotic arm 1 is a surgical passive arm, and the spherical second joint structure 14 has three degrees of freedom. Therefore, the surgical passive arm provided with the second joint structures 14 is flexible to operate when configured to be connected to the surgical tool or to fix the limb.

The above embodiments are merely used to illustrate the present invention, but not to limit the present invention. Although the present invention has been described in detail with reference to the embodiments, those of ordinary skill in the art should understand that various combinations, modifications or equivalent substitutions may be made to the technical solutions of the present invention without departing from the spirit and scope of the technical solutions of the present invention, and should be all included in the scope of claims of the present invention.

The invention claimed is:

1. A robotic arm, comprising:
   an upper arm and a front arm;
   a first joint structure, wherein the upper arm and the front arm are articulated together by the first joint structure;
   a second joint structure, arranged at an end of the upper arm and/or an end of the front arm;
   a first driving mechanism, arranged in the upper arm; and
   a second driving mechanism, arranged in the front arm,
   wherein the first joint structure comprises a first force amplification apparatus and a first locking element, the second joint structure comprises a second force amplification apparatus and a second locking element, and the first driving mechanism and the second driving mechanism apply an acting force to the first locking element and/or the second locking element by the first force amplification apparatus and/or the second force amplification apparatus.

2. The robotic arm according to claim 1, wherein the first joint structure comprises:
   a first joint head and a second joint head; and
   an articulated shaft, wherein the first joint head and the second joint head are connected by the articulated shaft;
   wherein the first locking element is arranged between the first joint head and the second joint head and is configured to lock the first joint head and the second joint head; and
   wherein the first force amplification apparatus is arranged on one side and/or two sides of the first locking element and is configured to apply an amplified acting force to the first locking element.

3. The robotic arm according to claim 1, wherein the second joint structure comprises:
   a joint housing; and
   a third joint head, arranged in the joint housing,
   wherein the second locking element is arranged in contact with the third joint head and is configured to lock the third joint head; and
   wherein the second force amplification apparatus is arranged at one end of the second locking element and is configured to apply an amplified acting force to the second locking element.

4. The robotic arm according to claim 3, wherein a structure being at least partially spherical is provided at one end of the third joint head, and a spherical structure being partially recessed inwards is provided at one end of the second locking element and cooperates with a portion in contact with the third joint head.

5. The robotic arm according to claim 1, wherein the first force amplification apparatus and/or the second force amplification apparatus are/is of a lever structure.

6. The robotic arm according to claim 5, wherein the first force amplification apparatus comprises a first rotary shaft and a first force amplification rod arranged on the first rotary shaft, and a distance between a force receiving end of the first force amplification rod and the first rotary shaft is greater than a distance between a force applying end of the first force amplification rod and the first rotary shaft.

7. The robotic arm according to claim 5, wherein the second force amplification apparatus comprises two second force amplification rods connected together by a second rotary shaft, and a distance between a force receiving end of each of the second force amplification rods and the second rotary shaft is greater than a distance between a force applying end of the second force amplification rod and the second rotary shaft.

8. The robotic arm according to claim 2, wherein the first locking element comprises two or more friction plates sleeved on the articulated shaft.

9. The robotic arm according to claim 3, wherein a ball joint pin is provided at the other end of the third joint head and extends out of the joint housing.

10. The robotic arm according to claim 1, wherein the driving mechanism is an electric push rod.

* * * * *